United States Patent [19]

Plyter

[11] Patent Number: 5,107,853

[45] Date of Patent: Apr. 28, 1992

[54] APPARATUS FOR DETERMINING SUCEPTIBILITY TO CARPAL TUNNEL SYNDROME

[75] Inventor: Walter J. Plyter, Maitland, Fla.

[73] Assignee: Daniels Manufacturing Corporation, Orlando, Fla.

[21] Appl. No.: 637,779

[22] Filed: Jan. 7, 1991

[51] Int. Cl.$^5$ .............................................. A61B 5/103
[52] U.S. Cl. ...................................... 128/774; 33/512
[58] Field of Search .................... 128/774, 779, 782; 33/511, 512

[56] References Cited

U.S. PATENT DOCUMENTS

| | | | |
|---|---|---|---|
| 610,097 | 8/1898 | DeSilva | 33/512 |
| 3,196,551 | 7/1965 | Provost et al. | 128/774 |
| 3,722,103 | 3/1973 | Gregoire | 33/512 |
| 4,220,163 | 9/1980 | Afzali | 128/774 |
| 4,605,486 | 8/1986 | Moroney et al. | 128/774 |

*Primary Examiner*—Max Hindenburg
*Attorney, Agent, or Firm*—James H. Beusse

[57] ABSTRACT

Apparatus for providing an indication of susceptibility of a person to incur carpal tunnel syndrome by establishing a ratio of thickness to width of the person's wrist. A generally L-shaped housing has a first slide member coupled to a first arm and a second slide member coupled to a second arm. Each of the slide members has an element extends substantially perpendicularly to a direction of sliding motion of a corresponding slide member. Each of the elements extends into a space between the arms about an included angle defined by a juncture of the arms and each of the slide members has overlapping edges at their respective ends adjacent the juncture of the arms. The overlapping edges define a line bisecting the juncture when the height to width ratio of an area defined by the extending elements and the arms of the housing is approximately 0.7. The overlapping edges define a point on a predetermined side of the line indicating a ratio greater than about 0.7 when the person has a relatively higher susceptibility to carpal tunnel syndrome.

3 Claims, 2 Drawing Sheets

APPARATUS FOR DETERMINING SUCEPTIBILITY TO CARPAL TUNNEL SYNDROME

The present invention relates to apparatus for determining the proclivity of an individual to carpal tunnel syndrome and, more particularly, to an apparatus for rapidly determining the squareness of an individual's wrist and potential susceptibility to the syndrome from such measurement.

BACKGROUND OF THE INVENTION

Carpal tunnel syndrome is a painful condition of the wrist and fingers usually experienced by workers who perform jobs requiring frequent, repetitive use of the hands and wrists. Medically, the condition is believed to derive from compression of the median nerve passing through the carpal canal. Carpal tunnel syndrome is characterized by pain and paresthesia in the sensory distribution of the median nerve in the hand. Symptoms include numbness, tingling, and painful burning of the fingers which can radiate up the forearm to the shoulder.

Recent studies have shown that some workers are more prone to develop carpal tunnel syndrome than others. These studies have linked the shape of a person's wrist to his/her proclivity to develop carpal tunnel syndrome. In particular, it has been determined that the more square the shape of the wrist, the higher the susceptibility to carpal tunnel syndrome. In general, the average person has a wrist in which the ratio of thickness to width is in the range of 0.55 to 0.6. Persons with more square wrists, i.e., those having thickness to width ratios of 0.7 or larger, are more likely to develop carpal tunnel syndrome. If such susceptible workers can be identified, alternatives can be developed to minimize the risk to those workers. It is therefore desirable to provide an apparatus for easily identifying workers having wrist configurations with a proclivity for carpal tunnel syndrome.

SUMMARY OF THE INVENTION

The present invention comprises an apparatus for quickly and easily providing an indication of the relative squareness of a person's wrist and relating that measurement to the proclivity to develop carpal tunnel syndrome. In one form, the invention comprises a generally L-shaped flat, hollow housing having a pair of sliding members each restrained for sliding motion within a respective arm of the housing. Each sliding member includes an elongate element extending out of the housing and toward the space defined within the included angle formed by the juncture of the arms of the housing. The elongate elements are so arranged that each is slidably engagable with the distal crease of a person's wrist placed with the area between the housing arms and in contact therewith. The sliding members have a length such that the ends thereof extend into that portion of the housing at the juncture of the two arms in an overlapping manner. The lengths are preferably adjusted so that the point at which the ends overlap at the center of the juncture corresponds to a ratio of 0.7 to 1.0 (thickness to width). Wrists of different sizes but having the same ratio will define a straight line extending diagonally through the juncture of the two housing arms and such line is preferably marked on a transparent cover overlaying at least the area of overlap of the sliding members. A wrist having a thickness to width ratio greater than 0.7 will result in an overlap point on one side of the marked line while wrist ratios less than 0.7 will be indicated on another side of the line. Accordingly, the apparatus can quickly and easily indicate proclivity for carpal tunnel syndrome.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1:
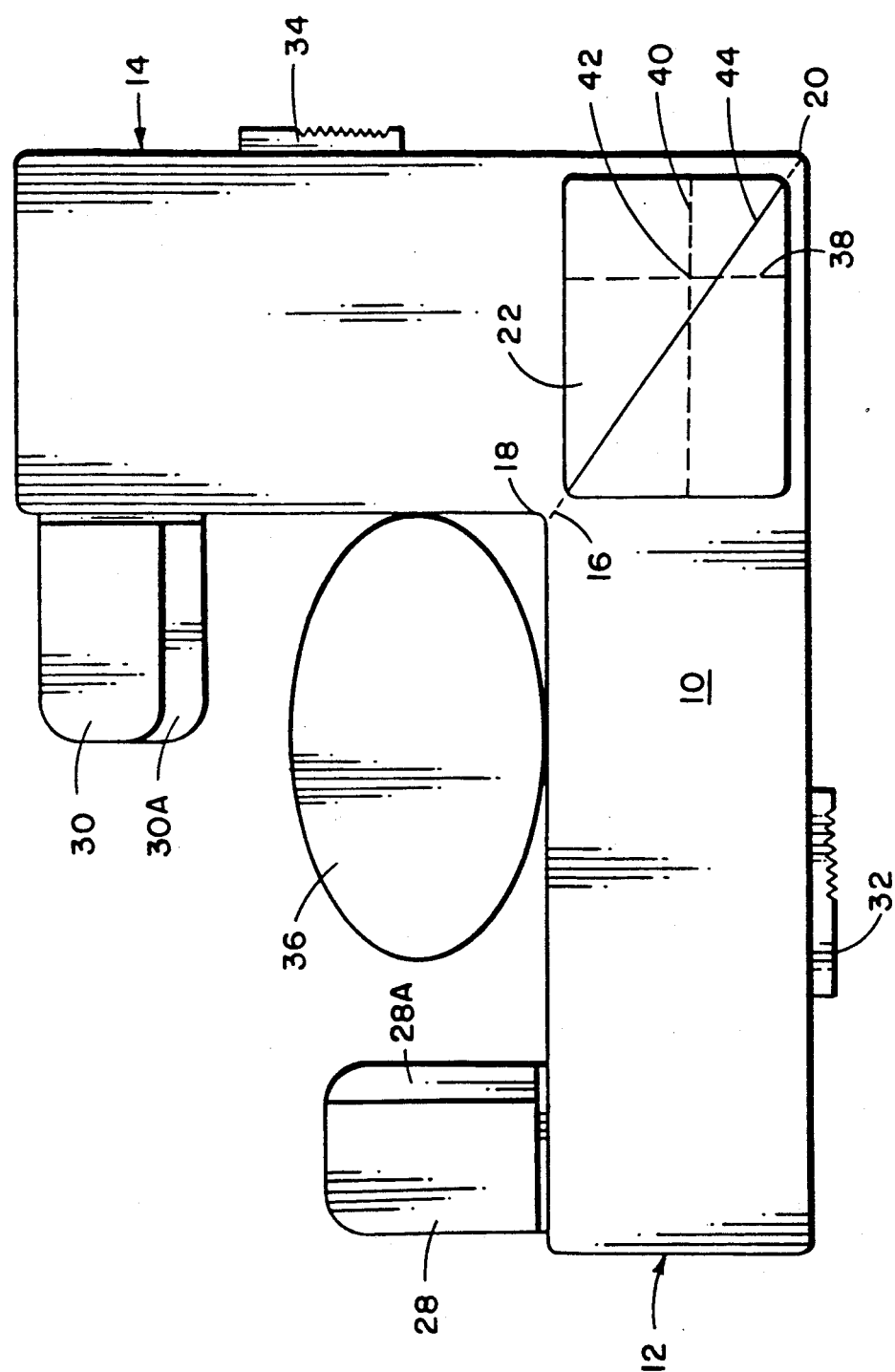
FIG. 1 is an elevation view of one form of apparatus in accordance with the present invention.

Referring now to FIG. 1, there is shown an elevation view of one form of apparatus in accordance with the present invention. The apparatus comprises a generally L-shaped housing 10 having a pair of generally right-angularly oriented arms 12 and 14. The arms 12, 14 form a juncture at 16 which, for purposes of description, will be assumed to lie along a diagonal extending from the inner included corner 18 to the outer corner 20. The front side of the apparatus, i.e., the side facing the viewer in FIG. 1, incorporates a transparent window 22 extending over the juncture 16.

The housing 10 is desirably hollow for accepting a pair of slide members 24 and 26 positioned respectively in arms 12 and 14 (shown in FIG. 2), which are slidably movable over a predetermined range. Slide member 24 includes a contact element 28 extending into the space between the arms 12 and 14 and about the included angle at corner 18. Similarly, slide member 26 includes a contact element 30 extending therefrom and into the same space generally perpendicular to element 28. Each of the contact elements 28 and 30 have a relatively thin leading edge portion 28A and 30A, respectively. The edge portions 28A and 30A are sized to fit into the distal crease of a person's wrist. Each of the slide members 24, 26 further include finger operable extensions 32, 34, respectively, protruding through elongated apertures in external edges of corresponding ones of the arms 12, 14. The extensions 32, 34 provide a convenient means of sliding members 24 and 26.

The oval shaped object 36 in FIG. 1 represents a cross-section of a person's wrist. As the extensions 32, 34 are manipulated to slide the members 24, 26, the leading edge portions 28A and 30A of the elements 28 and 30 are brought into engagement with the object 36. Viewing through the window 22, the ends 38 and 40 of the slide members can be seen to overlap forming a point 42 corresponding to the ratio of thickness to width of the object 36. In a preferred embodiment, the ends 38 and 40 are selected to intersect on a marked line 44 corresponding to a diagonal extending generally from corner 18 to corner 20 when the thickness to width ratio of object 36 is about 0.7. If the ratio of object 36 is greater than 0.7, the intersection of the ends 38 and 40 will occur on the right hand side of line 44 while ratios less than 0.7 will fall on the left hand side of line 44. Thus, the apparatus provides a rapid and easy method of determining proclivity for carpal tunnel syndrome.

Figure 2:
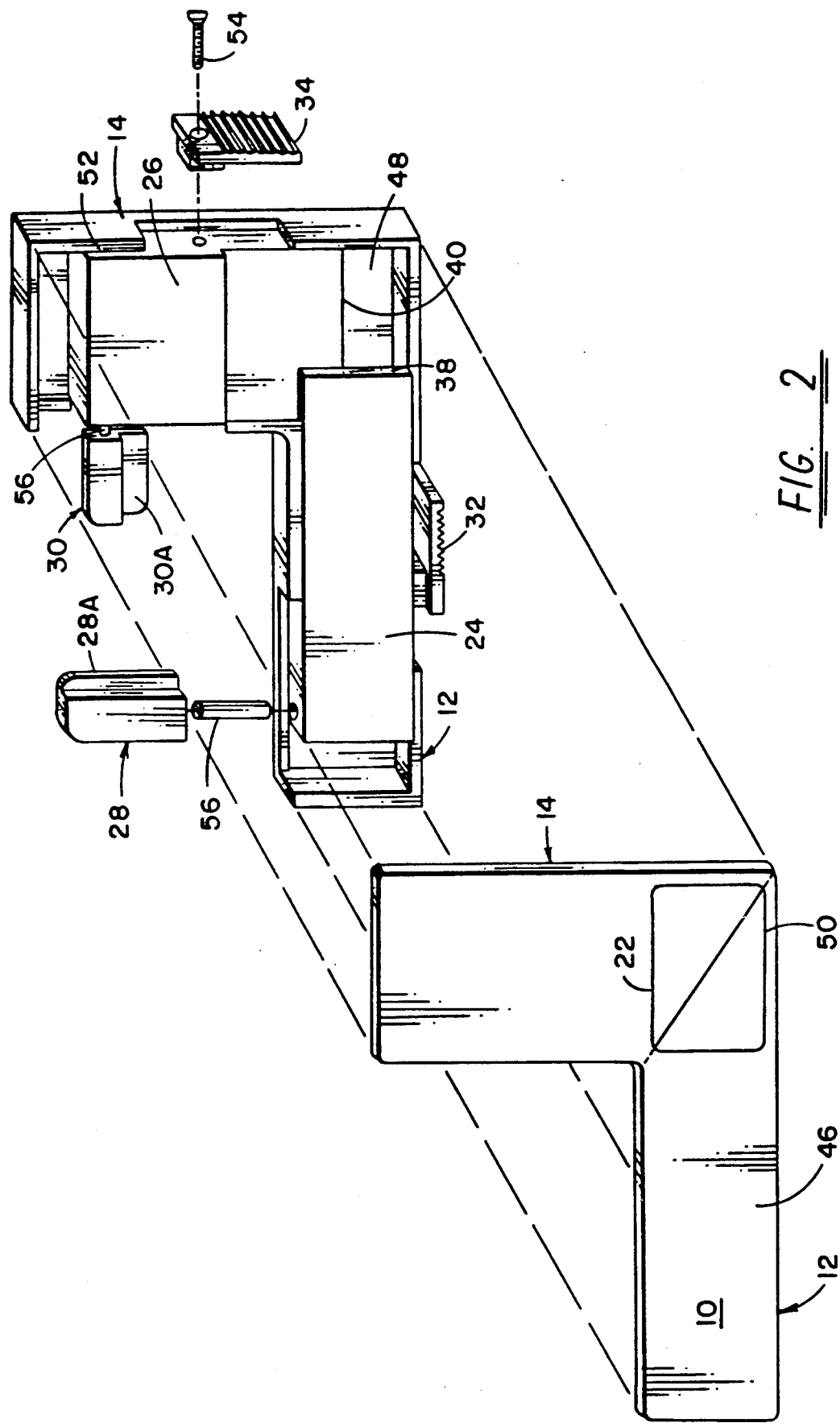
FIG. 2 is an exploded view of the apparatus of FIG. 1.

FIG. 2 is an exploded view of the apparatus of FIG. 1. The housing 10 comprises a bottom section 48 and a cover or top section 46. The top section 46 may be a flat plate with an aperture 50 at the juncture of the arms 12 and 14 in which the transparent window 22 may be installed by glue or other suitable means. Alternatively, the top section 46 could be formed of transparent plastic with reverse silk screening to color off areas to be dark or upon which printing is to be used. The window 22 could be left transparent or tinted one color on one side of line 44 and another color on an opposite side. Tinting would be light so that intersection point 42 is visible. The bottom section 48 is formed with upstanding side edges 52 for defining a channel-shaped configuration for receiving the sliding members 24 and 26. The members 24 and 26 have a thickness slightly less than the height of the edges 52 so that they are free to slide within the housing when section 46 is assembled on section 48. However, at their overlapping ends 38 and 40, the thickness of each slide member is reduced by half to maintain the total thickness and permitting overlapping, sliding motion.

The extensions 32, 34 may be attached to their respective slide members 24, 26 by an adhesive bond or by fastening with a threaded fastener 54 as is illustrated. The contact elements 28 and 30 may be attached to the slide members using pins 56 fitting between matching apertures in the respective element 28, 30 and slide member 24, 26 combination. In the case of both the elements 28, 30 and the extensions 32, 34, the edges 52 of the bottom section 48 are machined or formed with elongated slots to permit a preselected range of motion of the slide members 24, 26.

Considering FIGS. 1 and 2, it can be seen that a wrist placed in the inside corner of the apparatus can be readily measured by moving the sliding members 24, 26 until the leading edge portions 28A, 30A of the elements 28, 30 are in contact with the wrist at the distal crease. The point of intersection, indicated at 42, of the overlapping ends 38, 40 will fall either on line 44 or left or right of the line depending upon the ratio of thickness to width. Given this information, a person can make an informed decision regarding certain repetitive jobs depending upon their proclivity to carpal tunnel syndrome.

While the invention has been described in what is considered to be a preferred embodiment, other modifications and variations will become apparent to those skilled in the art. It is intended therefore that the invention not be unduly limited but be interpreted within the full spirit and scope of the appended claims.

What is claimed is:

1. Apparatus for providing an indication of susceptibility of a person to incur carpal tunnel syndrome by establishing a ratio of thickness to width of the person's wrist comprising a generally L-shaped housing having a first arm and a second arm, a first slide member coupled to said first arm and a second slide member coupled to said second arm, each of said slide members having an element extending substantially perpendicular to a direction of sliding motion of a corresponding slide member, each of said elements extending into a space between said arms about an included angle defined by a juncture of said arms, said slide members being held within said housing such that an end of one of said slide members overlaps an end of the other of said members adjacent said juncture of said arms, said overlapping ends defining a line bisecting said juncture when the height to width ratio of an area defined by said extending elements and said arms of said housing is approximately 0.7.

2. The apparatus of claim 1 wherein said overlapping ends define a point on a predetermined side of said line indicating a ratio greater than about 0.7 when the person has a relatively higher susceptibility to carpal tunnel syndrome.

3. Apparatus for determining the relative thickness to width ratio of a person's wrist comprising:
    a generally L-shaped housing having first and second arms extending from a common juncture;
    a first slide member slidingly coupled to said first arm and having an indicator means coupled thereto for providing a first indication of a dimension of a wrist in a first direction when the wrist is positioned in the juncture defined by the first and second arms and said first slide member is adjusted to indicate the dimension of the wrist in the first direction;
    a second slide member slidingly coupled to said second arm and having an indicator means coupled thereto for providing a second indication of a dimension of the wrist in a second direction when the wrist is positioned in the juncture and said second slide means is adjusted to indicate the dimension of the wrist in the second direction; and
    means comparing said first and second indication for providing a relative thickness to width determination.

* * * * *